(12) United States Patent
Guit et al.

(10) Patent No.: US 10,556,876 B2
(45) Date of Patent: Feb. 11, 2020

(54) PROCESS FOR THE PREPARATION OF GAMMA VALEROLACTONE FROM LEVULINIC ACID

(71) Applicant: DSM IP ASSETS B.V., Heerlen (NL)

(72) Inventors: Rudolf Philippus Maria Guit, Echt (NL); Alejandro Varela Fernández, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/552,006

(22) PCT Filed: Feb. 16, 2016

(86) PCT No.: PCT/EP2016/053267
§ 371 (c)(1),
(2) Date: Aug. 18, 2017

(87) PCT Pub. No.: WO2016/135009
PCT Pub. Date: Sep. 1, 2016

(65) Prior Publication Data
US 2018/0044310 A1    Feb. 15, 2018

(30) Foreign Application Priority Data

Feb. 24, 2015  (EP) .................................. 15156355
Feb. 24, 2015  (EP) .................................. 15156357

(51) Int. Cl.
*C07D 307/33*    (2006.01)

(52) U.S. Cl.
CPC ................................ *C07D 307/33* (2013.01)

(58) Field of Classification Search
CPC .................................................. C07D 307/33
See application file for complete search history.

(56) References Cited

U.S. PATENT DOCUMENTS

| 2,368,366 A | 1/1945 | Kyrides et al. |
| 2013/0296579 A1 | 11/2013 | Rode et al. |

FOREIGN PATENT DOCUMENTS

WO   WO 2012/175439   12/2012

OTHER PUBLICATIONS

Bond, J.Q., et al. "Analysis of Kinetics and Reaction Pathways in the Aqueous-Phase Hydrogenation of Levulinic Acid to Form γ-Valerolactone over Ru/C." (Feb. 28, 2014), ACS Catal. vol. 4, pp. 1171-1181. (Year: 2014).*
Horvath, I.T., et al. "γ-Valerolactone—a sustainable liquid for energy and carbon-based chemicals." Green Chemistry (2008), .vol. 10, pp. 238-242. (Year: 2008).*
"Encyclopedia of Chemical Engineering Equipment." (Mar. 4, 2014). Accessed Oct. 26, 2018. Available from: <http://encyclopedia.che.engin.umich.edu/Pages/SeparationsChemical/Strippers/Strippers.html > . (Year: 2014).*
University of York. "Recycling in the chemical industry." (Jan. 16, 2014). Accessed Oct. 26, 2018. Available from: < http://www.essentialchemicalindustry.org/processes/recycling-in-the-chemical-industry.ht >. (Year: 2014).*
International Search Report for PCT/EP2016/053267 dated Apr. 11, 2016, 4 pages.
Ramachandran et al., "Selective reductions", The Journal of Organic Chemistry, vol. 67, Jan. 1, 2002, pp. 5315-5319.
Al-Shaal et al., "Exploring the ruthenium catalyzed synthesis of [gamma]-valerolactone in alcohols and utilization of mild solvent-free reaction conditions", Green Chemistry, vol. 14, No. 5, Jan. 1, 2012, pp. 1260-1963.
Manzer, "Catalytic synthesis of alpha-methylene-gamma-valerolactone: a biomass-derived acrylic monomer", Applied Catalysis A: General, Elsevier Science, vol. 272, No. 1-2, Sep. 28, 2004, pp. 249-256.
Wright et al., "Development of Heterogeneous Catalysts for the Conversion of Levulinic Acid to γ-Valerolactone", ChemSUSChem, 2012, pp. 1657-1667.

* cited by examiner

*Primary Examiner* — Andrew D Kosar
*Assistant Examiner* — John S Kenyon
(74) *Attorney, Agent, or Firm* — Nixon & Vanderhye P.C.

(57) ABSTRACT

The invention relates to process for the preparation of gamma valerolactone (GVL) from levulinic acid (LA), said process comprising a) subjecting LA to a hydrogenation reaction comprising hydrogen and a solid catalyst system comprising a metal and a support in the liquid phase, to yield a first reaction mixture comprising GVL, hydroxypentanoic acid (4HPA), and water; b) removing water from said first reaction mixture; and c) subjecting the mixture obtained in step b) to a further reaction under conditions suitable to convert said 4-HPA to GVL, to yield a further reaction mixture. Steps b) and c) can be integrated. Optionally, water can be removed from the further reaction mixture. The process may include recycling the—optionally at least partially dewatered—further reaction mixture back to step (b). This is particularly advantageous when the first reaction mixture is low in, or even free of levulinic acid. Alternatively, the further reaction mixture or at least partially dewatered further reaction mixture can be submitted to a distillation step, whereby the distillate can be collected to recover GVL.

15 Claims, 1 Drawing Sheet

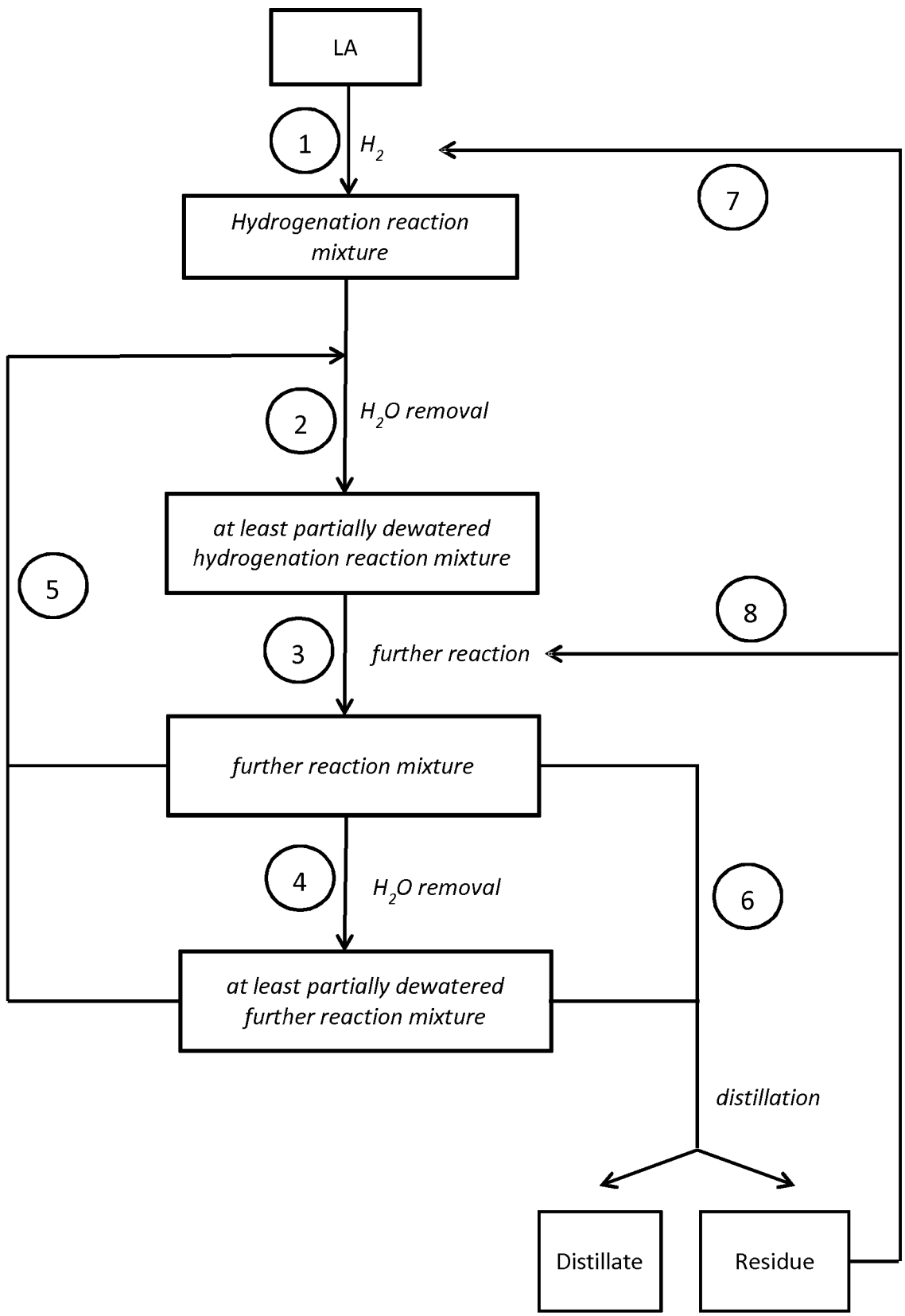

PROCESS FOR THE PREPARATION OF GAMMA VALEROLACTONE FROM LEVULINIC ACID

This application is the U.S. national phase of International Application No. PCT/EP2016/053267 filed Feb. 16, 2016 which designated the U.S. and claims priority to EP Patent Application No. 15156355.8 filed Feb. 24, 2015 and EP Patent Application No. 15156357.4 filed Feb. 24, 2015, the entire contents of each of which are hereby incorporated by reference.

FIELD OF THE INVENTION

This invention relates to a process for the preparation of gamma valerolactone from levulinic acid.

BACKGROUND OF THE INVENTION

Gamma-valerolactone (GVL, 5-methylbutyrolactone) is a valuable compound which can be used in the production of adipic acid (1,6-hexanedioic acid) which is an important precursor for inter alia the production of polyamides such as polyamide 6,6 or polyamide 4,6 (also referred to as "Stanyl"). Hydrogenation of levulinic acid to produce GVL is described in L. E. Manzer, Appl. Catal. A, 2004, 272, 249-256; J. P. Lange, J. Z. Vestering and R. J. Haan, Chem. Commun., 2007, 3488-3490; R. A. Bourne, J. G. Stevens, J. Ke and M. Poliakoff, Chem. Commun., 2007, 4632-4634; H. S. Broadbent, G. C. Campbell, W. J. Bartley and J. H. Johnson, J. Org. Chem., 1959, 24, 1847-1854; R. V. Christian, H. D. Brown and R. M. Hixon, J. Am. Chem. Soc., 1947, 69, 1961-1963; L. P. Kyrides and J. K. Craver, U.S. Pat. No. 2,368,366, 1945; H. A. Schuette and R. W. Thomas, J. Am. Chem. Soc., 1930, 52, 3010-30121; WO2012/175439; US2006/0100449; and US2003/0055270.

SUMMARY OF THE INVENTION

The invention relates to process for the preparation of gamma valerolactone (GVL) from levulinic acid (LA), said process comprising the steps of:
(a) subjecting LA to a hydrogenation reaction comprising hydrogen and a solid catalyst system comprising a metal and a support in the liquid phase, to yield a first reaction mixture comprising GVL, hydroxypentanoic acid (4HPA), and water;
(b) removing water from said first reaction mixture; and
(c) subjecting the mixture obtained in step b) to a further reaction under conditions suitable to convert said 4-HPA to GVL, to yield a further reaction mixture.

Steps b) and c) can be integrated. Optionally, water can be removed from the further reaction mixture. The process may include recycling the—optionally at least partially dewatered—further reaction mixture back to step (b). This is particularly advantageous when the first reaction mixture is low in, or even free of levulinic acid. Alternatively, the further reaction mixture or at least partially dewatered further reaction mixture can be submitted to a distillation step, whereby the distillate can be collected to recover GVL. In addition, the distillation residue can be recycled to the hydrogenation step. The distillation and recycle of the residue to the hydrogenation are particularly advantageous when the first reaction mixture comprises levulinic acid. Said distillation step, when done at low temperature, followed by recycling at least part of the distillation residue back to the hydrogenation prevents problems in distillation caused by levulinic acid, and increases the yield of GVL. The presence of GVL in the distillation residue is preferred, in order to keep the temperature in the residue low.

DETAILED DESCRIPTION OF THE INVENTION

In a first aspect the invention relates to a process for the preparation of gamma valerolactone (GVL) from levulinic acid (LA), said process comprising the steps of:
(a) subjecting LA to a hydrogenation reaction comprising hydrogen and a solid catalyst system comprising a metal and a support in the liquid phase, to yield a first reaction mixture comprising GVL, hydroxypentanoic acid (4HPA), and water;
(b) removing water from said first reaction mixture; and
(c) subjecting the mixture obtained in step b) to a further reaction under conditions suitable to convert said 4-HPA to GVL, to yield a further reaction mixture.

Step (a)—Hydrogenation

In the first step of the process of the invention LA is hydrogenated in the presence of hydrogen and a solid catalyst system comprising a metal and a support in the liquid phase to yield a first reaction mixture.

LA is a starting molecule for the synthesis of commercially important compounds. Commercially, LA is made from furfuryl alcohol. It is also possible to produce LA by acid hydrolysis of biomass, see for example U.S. Pat. Nos. 5,608,105, 8,138,371, US2010/312006, U.S. Pat. Nos. 4,897,497, 6,054,611, and "The Biofine Process—Production of Levulinic Acid, Furfuraldehyde, and Formic Acid from Lignocellulosic Feedstocks", D. J. Hayes, S. Fitzpatrick, M. H. B. Hayes, J. R. H. Ross, in Biorefineries—Industrial Processes and Products, Status Quo and Future Directions, B. Kamm, P R. Gruber, M. Kamm, eds., Wiley-VCH, Weinheim, Germany, 2010, p 139-164. When LA is produced from furfuryl alcohol, it can be isolated e.g. by distillation. The LA in the process of the invention may be an isolated preparation obtained from any of these processes, or from other LA processes not described here.

The metal is preferably selected from Pt, Pd, and/or Ru, and is most preferably Ru. The metal is preferably supported on a solid support, e.g. on C, $ZrO_2$, or $TiO_2$.

The amount of catalyst to be used is not critical. Typically in a slurry phase hydrogenation process the catalyst contains between 0.1 and 10 wt % (preferably 0.5-5 wt %) metal and the amount of catalyst including support is generally in the range of 0.1 to 10 wt % (preferably 1-5 wt %) based on the liquid phase present in the reactor. Preferably the amount of catalytic metal is between 2.5 and 2,000 ppm. The process of the invention may be carried out using a solvent.

The temperature at which the hydrogenation reaction in step (a) is carried out is not critical and may be anywhere between 50 and 250° C., more preferably between 90 and 200° C. Preferably a temperature of between 100 and 180° C. is used. Lower temperatures are desired due to cost considerations and equipment requirements. If the temperature is too high, e.g. more than 180° C., selectivity and catalyst stability may decrease. If the temperature is too low, e.g. below 100° C., reactors become very big (high investment) and heat integration may be less efficient.

The pressure at which the hydrogenation reaction is carried out is also not critical, but it may be advantageous to carry out the process at lower pressure. Preferably the pressure is between 1-100 bar, more between preferably 5-50 bar, even more preferably between 10-30 bar.

The hydrogenation reaction may be carried out as (repeated) batch process, a repetitive batch process, or more preferred as a continuous process. If the process is carried out as a batch process, it is carried out for a length of time such that a large part of LA has been converted. The skilled person can simply monitor the (remaining) amount of LA during the course of the hydrogenation reaction and proceed with step (b) after a target conversion per pass is reached, for example 50% or more, or 60% or more, preferably 70% or more, more preferably 80% or more, even more preferably 90% or more. The conversion per pass is preferably between 60% and 98%, more preferably between 60% and 95%.

In an embodiment, the hydrogenation reaction is complete, or nearly complete, for example at least 80%, or at least 90%, even more preferably at least 95%, at least 98% of the LA is converted, most preferably all LA has been converted in the hydrogenation step.

In an another embodiment, the hydrogenation reaction is incomplete (i.e. the conversion is less than 100%) and the first reaction mixture also comprises LA.

The skilled person can monitor the amount of residual LA by using analysis methods like HPLC, GC/MS and $^1$H-NMR.

The reactor for the hydrogenation reactor may be a well-mixed reactor (CSTR, bubble column, etc.) or a staged reactor (multiple CSTR's or bubble columns in series).

The amount of water present in the first reaction mixture may range between 5-50% w/w, preferably the amount of water is less than 50%, more preferably less than 30%, more preferably less than 20%. The residence time in the reactor may be from 0.1-10 hour.

The first reaction mixture comprises hydroxypentanoic acid (4-HPA). Al-Saal et al. (*Green Chem.*, 2012, 14, 1260) show a reaction pathway for the hydrogenation of LA to GVL where hydroxypentanoic acid (4-HPA, or γ-hydroxy-valeric acid) is a possible intermediate. However, the presence of 4-HPA in the final product has never been disclosed in the state of the art. Indeed, the state of the art reports that up to 100% selectivity/yield can be achieved. Thus, the person skilled in the art would expect the end-product to consist of 100% GVL. The inventors realized that the presence of 4-HPA causes a loss in GVL yield.

Steps (b) and (c) may be integrated. Step c) is preferably carried out separately from step a).

Prior to water removal, a vapour phase (comprising $H_2$) can be removed from the first reaction mixture. Removed $H_2$ can be recovered and recycled.

Step (b)—Water Removal

In step (b) water is removed from the first reaction mixture obtained in step (a). Water is removed in order to prevent the presence of water in a subsequent distillation top fraction together with GVL.

Water is preferably removed in a distillation step. This may be done in a distillation column with or without a reflux. If the distillation column has no reflux it may also be called a water stripper column. In the process of the invention water may alternatively be removed in an alternative strip process using an inert gas as sweeping gas for water. In order to keep investment low and in order to keep residence time of products short at the relatively high temperatures of the distillation process, the person skilled in the art would design a continuously operated distillation/stripper column in a way that residence times are generally less than 30 minutes. Most of the time liquid residence times are in the range of 2 to 20 minutes.

The skilled person typically refers to removal of water as "stripping", and in the context of this invention "stripping" shall refer to the removal of water. Likewise, "stripper" shall refer to the equipment used to remove the water. Stripping is preferably done at 130° C. or lower, or 120° C. or lower, or 110° C. or lower, at a pressure that is sufficient to remove water at the mentioned temperatures. The skilled knows how to set the pressure to achieve this. The water removal in step (b) is preferably done under conditions suitable to convert said 4-HPA to GVL (see below).

Step (c)—Further Reaction

In step (c) the first reaction mixture obtained in step (b) is subjected to a further reaction under conditions suitable to convert said 4-HPA to GVL, to yield a further reaction mixture. The conversion rate of 4-HPA to GVL will substantially increase once water is removed. The conversion rate may be further increased by further raising the temperature in the further reaction. The conversion rate may also be enhanced by using an acidic homogeneous or heterogeneous catalyst, as for instance sulphuric acid or phosphoric acid, or alternatively by using an acidic solid catalyst like for instance ZSM5. Different types of after-reactors may be used which may have well-mixed or plug-flow characteristics. Plug-flow characteristics will enhance the conversion rate.

The further reaction is preferably carried out in a separate reactor. The stream from the water removal step (b) may comprise GVL and 4-HPA, and is preferably free of water. It may comprise (unreacted) levulinic acid.

During removal of water, but prior to the further reaction, conversion of 4-HPA to GVL may already take place. However, when using strippers generally known in the art, with a residence time of typically 2-20 minutes, 4-HPA will only be converted partially. Thus, if conversion of LA to GVL were done with a process having a hydrogenation step and a water removal step, but without a further reaction, less GVL would be produced per pass, and a relatively large amount of 4-HPA must finally be recycled as bottom product from step (c) to step (a) (higher investment/more energy).

Step (c) is preferably carried out at low temperature, preferably at 130° C. or lower, more preferably 120° C. or lower, such as between 50 and 140° C., preferably between 90 and 130° C., more preferably between 100 and 120° C. Too high temperature, e.g. 130° C. or more, may lead to undesired conversion of LA to angelica lactone.

The pressure in step (c) is preferably pressure, preferably 50 mbar or less, more preferably 30 mbar or less, even more preferably 20 mbar or less, or even 10 mbar or less.

Optionally an acidic catalyst may be used in further reaction to reduce the residence time needed. The further reaction may be carried out in a well-mixed reactor, or a plug flow type of reactor. In an embodiment, prior to step c) the solid catalyst is removed from the first reaction mixture. In an embodiment, the further reaction may be carried out in a separate unit than the water removal step. The separate unit may comprise an acidic catalyst. Alternatively, the further reaction may be carried out in the same unit as the water removal step. For example, water can be removed in a stripper with an extended bottom volume to allow sufficient conversion of 4-HPA to GVL. In this embodiment, the water removal and the further reaction step (c) may take place in one and the same unit.

The skilled person will appreciate that conversion of 4-HPA to GVL may occur during water removal, as is explained above. Thus, water removal and a further reaction may overlap, or even coincide. In the context of this invention, even if 4-HPA to GVL conversion takes place entirely during water removal, the process of the invention may intrinsically include a further reaction.

During the further reaction not necessarily all 4-HPA is converted to GVL. Preferably at least 50%, at least 60%, more preferably at least 70, 80% of the 4-HPA is converted to GVL in the further reaction, based on the amount of 4-HPA present in the first reaction mixture. Most preferably essentially all 4-HPA is converted to GVL.

The further reaction mixture will comprise GVL. The GVL may be pure enough such that a further isolation step is not required. If desired, the GVL can be isolated by a further isolation step, such as distillation, for example if the further reaction mixture comprises LA and/or 4-HPA.

In an embodiment, the further reaction mixture is low in LA, for example the further reaction mixture may comprise 10 wt % LA or less, based on the total weight of the mixture, more preferably the further reaction mixture comprises 5 wt % LA or less, more preferably 2 wt % LA or less, even more preferably the further reaction mixture is free of LA.

In an embodiment, the process further comprises the step of:
d) removing water from the further reaction mixture, to yield an at least partially dewatered further reaction mixture.

Step (d) is particularly advantageous if the further reaction mixture comprises water, and/or if the presence of water in the end product (GVL) is not desired. Steps (b), (c) and (d) may be integrated.

In an embodiment, the process comprises:
recycling the—optionally at least partially dewatered—further reaction mixture back to step (b).

This recycle step may be advantageous in order to avoid a water removal unit step (d). It is also advantageous if the conversion in the hydrogenation reaction is (nearly) complete, and/or if the—optionally at least partially dewatered further reaction mixture is low in LA, or even free of LA. In this scenario, and/or if some water is allowed in the end product (VL), step (d) may be omitted.

In an other embodiment, the process comprises:
subjecting the—optionally at least partially dewatered—further reaction mixture to a distillation step to yield a distillate and a distillation residue; and
recycling at least part of said distillation residue from back to step (a).

The inventors have found that if the conversion of LA to GVL is incomplete, any remaining LA in the first reaction mixture or in the—optionally at least partially dewatered—further reaction mixture may cause problems in a subsequent distillation. When the further reaction is subjected to a distillation under normal conditions, that is, such that GVL is in the distillate and LA and 4HPA are in the distillation residue, the GVL yield may be insufficient. The inventors have developed an efficient process to prepare GVL from LA whereby the further—optionally dewatered—further reaction mixture is subjected to a distillation, followed by recycling at least part of the distillation residue back to step (a).

The distillation is preferably done such that the distillate comprises GVL and the distillation residue comprises LA. The distillation residue may optionally comprise GVL. If the further reaction mixture comprises 4-HPA, said 4-HPA may end up in the distillation residue, together with LA. Thus, the distillation residue optionally comprises 4-HPA. The presence of GVL in the distillation residue may be beneficial to keep the temperature in the residue low.

The distillation is preferably carried out at a pressure of 10 bar or less, more preferably 50 mbar or less, even more preferably 30 mbar or less, 20 mbar or less, even more preferably 10 mbar or less, preferably such that GVL is in the bottom at an amount such that the temperature is preferably 130° C. or lower, more preferably 120° C. or less, and at low pressure, preferably 50 mbar or less, more preferably 30 mbar or less, even more preferably 20 mbar or less, or even 10 mbar or less. Such amount of GVL is typically between 10 and 60%. These distillation conditions are advantageous to increase GVL yield. The inventors hypothesized that higher distillation temperatures result in formation of angelica lactone which will end up in the distillate and will result in impure GVL. This is highly undesirable. Lower distillation temperatures may prevent formation of angelica lactone.

At least part of the distillation residue is recycled to step (a). Preferably most, or even (essentially) all of the distillation residue is recycled to step (a). Thus any LA, 4-HPA, and/or GVL present in the distillation residue is not lost, and any LA and/or 4-HPA can be converted to GVL in a (subsequent) further reaction. In the event that the distillation residue comprises 4-HPA, recycling said distillation residue may increase GVL yield, as no or less 4-HPA will be lost. Thus, recycling may increase the yield of GVL via 4-HPA and/or LA.

In an other embodiment, the process comprises:
subjecting the—optionally at least partially dewatered—further reaction mixture to a distillation step to yield a distillate and a distillation residue; and
recycling at least part of said distillation residue from back to step (c).

The invention also provides a process for the preparation of gamma valerolactone (GVL) from levulinic acid (LA), said process comprising the steps of:
(a) subjecting LA to a hydrogenation reaction comprising hydrogen and a solid catalyst system comprising a metal and a support in the liquid phase, to yield a first reaction mixture comprising at least GVL and hydroxypentanoic acid (4HPA), and water;
(b) removing water from the first reaction mixture;
(c) subjecting the mixture obtained in step b) to a further reaction under conditions suitable to convert said 4-HPA to GVL, to yield a further reaction mixture;
(d) optionally removing water from the further reaction mixture;
(e) subjecting the further reaction mixture obtained in step (c) or step (d) to a distillation step to yield a distillate comprising GVL and a distillation residue;
(f) recycling at least part of said distillation residue back to step (a).

LEGEND TO THE FIGURE

FIG. 1 is a flow diagram illustrating the steps of an example of a reactor layout for the process of the invention.
1. Hydrogenation of levulinic acid, resulting in a first reaction mixture comprising GVL, 4-HPA, and water. The first reaction mixture may optionally comprise levulinic acid, when the hydrogenation reaction is incomplete.
2. Water removal from the first reaction mixture, resulting in an at least partially dewatered first reaction mixture.
3. A further reaction under conditions suitable to convert 4-HPA to GVL, to yield a further reaction mixture.
4. Optional water removal from the further reaction mixture, to yield an at least partially dewatered further reaction mixture.
5. The further reaction mixture and/or at least partially dewatered further reaction mixture can be recycled to the water removal step. This step is advantageous when the first reaction mixture is low in levulinic acid, or even free in levulinic acid.

6. Alternatively, the further reaction mixture and/or at least partially dewatered further reaction mixture can be submitted to a distillation step, whereby the distillate can be collected to recover GVL.
7. In addition, the distillation residue can be recycled to the hydrogenation step. Steps 6 and 7 are particularly advantageous when the first reaction mixture comprises levulinic acid.

EXAMPLES

Levulinic Acid was obtained from Acros Organics, Geel, Belgium. Gamma valerolactone was measured by GC analysis using cyclohexylbenzene as an external standard. Escat 4401, CAS [7740-18-8] (reduced) containing 5% Ru/C (Ru:C ratio, 1:20) and 58.45% water, was purchased from Strem Chemicals, Newburyport, Mass., USA.

Example 1

A 150 mL autoclave (Parr Instrument Company, Moline, Ill., USA) was charged with levulinic acid (80 g, 0.68 mol), water (0.80 g, 0.44 mol) and 5 w % Ru/C catalyst (0.80 g). Then the autoclave was purged 3 times with nitrogen and subsequently 3 times with hydrogen. The autoclave was stirred at 1500 RPM, pressurized to 2.06 MPa hydrogen and heated up to 110° C. Next, samples were taken in time. Reaction products have been analyzed by GC/MS and $^1$H-NMR. After 45 min complete conversion of levulinic acid and 93% yield to gamma-valerolactone were obtained. $^1$H-NMR analysis showed 7% yield to 4-hydroxypentanoic acid. The water content of the product mixture was determined to be 15 w % using (Karl-Fischer titration method).

Example 2

After taking the last sample at 45 minutes reaction time in the experiment of Example 1, the liquid content of the reactor was pushed out by overpressure through a filter to remove the catalyst and directly cooled down to room temperature and depressurized to atmospheric conditions. 30 g of the harvested liquid reaction product was fed to a 100 ml thermostated glass vessel. The vessel was connected to a vacuum system and under stirring the vessel content was heated-up to 110° C. The vessel was kept for 30 min at those conditions in order to drive out as much as possible the water that was originally present in the feed and the chemically produced water. After 30 minutes the vessel was brought back to atmospheric conditions and the contents were quickly cooled down to room temperature. Analysis of the obtained product by GC/MS and $^1$H-NMR showed the final yield towards gamma-valerolactone was 98.2% and the final yield to 4-hydroxypentanoic acid was 1.8%.

Example 3

In parallel to Example 2 another 30 g of catalyst-free reaction product originating from example 1 was fed to a second 100 ml thermostated glass vessel and the same procedure was applied as described in Example 2. The only difference was that also 0.30 g Zeolite ZSM5 was added before the vacuum system was connected to the vessel. Now after 30 minutes of stirring at 110° C. and under vacuum the finally obtained yield to gamma-valerolactone was 99.6% and to 4-hydroxypentanoic acid 0.4%.

Example 4

A mixture of 300.2 g containing 75 wt % GVL, 14 wt % LA and 11 wt % water was fed to a Spalt column having 25 stages. A batch distillation was carried out at approx. 20 mbar head pressure. In the first distillation fractions mainly water was removed. The harvested GVL top product was essentially free of other organic impurities until 58% of all GVL in the original feed was distilled. At that point top and bottom temperature of the distillation column were 84 and 108° C. respectively. In the next distillation fractions other organic impurities appeared in the distillation product until 77%. Chemical analysis showed this product was mainly angelica lactone, which is a dehydration product of LA. Angelica lactone has a lower boiling point than GVL and will contaminate the GVL product. The table shows all further distillation fractions obtained. Table 1 shows that still high purity GVL was obtained after 77% of all GVL was distilled. The bottom temperature of the distillation was then 113° C. After the next distillation fraction 89% of all GVL was distilled and a bottom temperature of 129° C. was reached. Considering the Angelica lactone impurity level of 0.69 wt % in this fraction a bottom temperature of 129° C. may be considered close to critical for GVL purification and for LA loss due to LA dehydration reactions. The next fraction shows the undesired LA dehydration reaction further accelerates at even higher bottom temperatures leading to off-spec GVL and large LA losses due to angelica lactone formation.

TABLE 1

| GVL distilled over the top [% of feed] Calculated based on analyzed products | Angelica lactone in GVL top product | Levulinic acid in GVL top product | Bottom temperature [° C.] |
| --- | --- | --- | --- |
| Fraction 0-58 | 0 | 0 | 108 |
| Fraction 58-77 | 116 ppm | 0 | 113 |
| Fraction 77-89 | 0.69 w % | 0 | 129 |
| Fraction 89-96 | 5.70 w % | 0 | 151 |
| Fraction 96-98 | 64.7 w % | 131 | 153 |
| Fraction 98-99 | 83.7 w % | 0.2 w % | 154 |

The invention claimed is:
1. A process for preparing gamma valerolactone (GVL) from levulinic acid (LA), said process comprising the steps of:
   a) subjecting LA to a hydrogenation reaction at a temperature between 100 and 180° C. in the presence of hydrogen and a solid catalyst system comprising a metal and a support in the liquid phase to yield a first reaction mixture comprising GVL, hydroxypentanoic acid (4HPA), and water;
   b) removing water from said first reaction mixture by subjecting the first reaction mixture to distillation or stripping to obtain a dewatered mixture; and
   c) subjecting the dewatered mixture obtained in step b) to a further reaction at a temperature of 90 to 130° C. and in the presence of an acidic, homogeneous or heterogeneous catalyst to convert the 4-HPA in the dewatered mixture to GVL to thereby obtain a further reaction mixture.
2. The process according to claim 1, wherein step b) and step c) are integrated.
3. The process according to claim 1, wherein step (c) is carried out at a temperature of between 100 and 120° C. and at pressure of 50 mbar or less.
4. The process according to claim 1, wherein step c) is carried out separately from step a).
5. The process according to claim 1, wherein prior to step c) the solid catalyst is removed from the first reaction mixture.

6. The process according to claim 1, wherein the metal in step (a) is selected from Pt, Pd, and/or Ru.

7. The process according to claim 1, wherein the metal is supported on a solid support.

8. The process according to claim 1, wherein the process further comprises:
   d) removing water from the further reaction mixture, to yield an at least partially dewatered further reaction mixture.

9. The process according to claim 8, wherein steps b), c), and d) are integrated.

10. The process according to claim 1, wherein the process further comprises recycling the further reaction mixture back to step (b).

11. The process according to claim 1, wherein the process further comprises:
   (i) subjecting the further reaction mixture to a distillation step at a temperature below 130° C. to yield a distillate and a distillation residue; and
   (ii) recycling at least part of said distillation residue back to step (a).

12. The process according to claim 8, wherein the process further comprises recycling the at least partially dewatered further reaction mixture back to step (b).

13. The process according to claim 8, wherein the process further comprises:
   (i) subjecting the at least partially dewatered further reaction mixture to a distillation step at a temperature below 130° C. to yield a distillate and a distillation residue; and
   (ii) recycling at least part of said distillation residue back to step (a).

14. A process for preparing gamma valerolactone (GVL) from levulinic acid (LA), said process comprising the steps of:
   a) subjecting LA to a hydrogenation reaction at a temperature between 100 and 180° C. in the presence of hydrogen and a solid catalyst system comprising a metal and a support in the liquid phase to yield a first reaction mixture comprising GVL, hydroxypentanoic acid (4HPA), and water;
   b) removing water from the first reaction mixture to obtain a dewatered mixture;
   c) subjecting the dewatered mixture obtained in step b) to a further reaction at a temperature of 90 to 130° C. and in the presence of an acidic, homogeneous or heterogeneous catalyst to convert the 4-HPA in the dewatered mixture to GVL to thereby obtain a further reaction mixture;
   d) optionally removing water from the further reaction mixture;
   e) subjecting the further reaction mixture obtained in step (c) or step (d) to a distillation step at a temperature below 130° C. to yield a distillate comprising GVL and a distillation residue; and
   f) recycling at least part of the distillation residue from step e) from back to step (a).

15. The process of claim 14, wherein the yield of GVL obtained by the process is between 93% to 99.6%.

* * * * *